(12) United States Patent
Deskiewicz

(10) Patent No.: US 8,308,756 B1
(45) Date of Patent: Nov. 13, 2012

(54) RING REMOVER DEVICE AND METHOD

(76) Inventor: Al Deskiewicz, Bothell, WA (US)

(\*) Notice: Subject to any disclaimer, the term of this patent is extended or adjusted under 35 U.S.C. 154(b) by 369 days.

(21) Appl. No.: 12/660,880

(22) Filed: Mar. 5, 2010

Related U.S. Application Data

(60) Provisional application No. 61/159,304, filed on Mar. 11, 2009.

(51) Int. Cl.
*A61B 17/00* (2006.01)

(52) U.S. Cl. .................................................. 606/201

(58) Field of Classification Search .......... 606/201–204; 602/75, 20–22, 901, 5; 128/878–880, 898
See application file for complete search history.

(56) References Cited

U.S. PATENT DOCUMENTS

| | | | | |
|---|---|---|---|---|
| 2,456,507 | A * | 12/1948 | Hendrickson et al. | 602/63 |
| 4,441,489 | A * | 4/1984 | Evans et al. | 602/22 |
| 4,644,941 | A * | 2/1987 | Ogle, II | 602/22 |
| 4,813,406 | A * | 3/1989 | Ogle, II | 602/22 |
| 5,230,699 | A * | 7/1993 | Grasinger | 602/22 |
| 5,346,462 | A * | 9/1994 | Barber | 602/22 |
| 6,925,917 | B2 * | 8/2005 | Tilley et al. | 83/15 |
| 2004/0138598 | A1* | 7/2004 | Kortuem et al. | 602/22 |
| 2005/0027223 | A1* | 2/2005 | Nguyen | 602/23 |

OTHER PUBLICATIONS

Cresap, Charles R., Removal of a Hardened Steel Ring from an Extremely Swollen Finger, May 1995, American Journal of Emergency Medicine, vol. 13, No. 3, pp. 318-320.*
Cluett, Jonathon, Finger Arthritis, Jan. 2, 2009, About.com Orthopedics, http://orthopedics.about.com/od/fingerconditions/a/fingerarthritis.htm.*
Crank, Josh, How to Remove a Stuck Ring on a Finger, Dec. 8, 2008, eHow.com, http://web.archive.org/web/20081226050358/http://www.ehow.com/how_4494806_remove-stuck-ring-finger.html.*
Wayback Machine, http://wayback.archive.org/web/20080815000000*/htto://www.ehow.com/how_4494806_remove-stuck-ring-finger.html.*
Rogers,Bhaheetharan,Allee and Noel—Ring Removal Device, Feb. 24, 2006, all pages, http://homepages.cae.wisc.edu/~bme402/ring_remover_s06/reports/Ring_Removal_Device_2.3.ppt, Madison, WI.
Rogers,Bhaheetharan,Allee and Noel—Destructive and Non-destructive Ring Removal Device, Apr. 28 2006, all pages, http://homepages.cae.wisc.edu/~bme402/ring_remover_s06/reports/BME_301-_Final_Paper_2.0.pdf, Madison, WI.

\* cited by examiner

*Primary Examiner* — Elizabeth Houston
(74) *Attorney, Agent, or Firm* — Bruce L Johnson

(57) ABSTRACT

A procedure and a medical kit for removing a ring from a swollen finger are described. The kit includes a panel set, a compression tape, and a compression tape puller. The panel set encircles the swollen finger with a cylindrical assembly that decreases in diameter when wrapped by said compression tape, forcing excess fluid from said swollen finger back into the hand. Swelling is thereby reduced allowing for removal of the ring.

18 Claims, 4 Drawing Sheets

RING REMOVER DEVICE AND METHOD

CROSS-REFERENCE TO RELATED APPLICATIONS

This application claims the benefit of provisional application 61/159,304 filed Mar. 11, 2009.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

BACKGROUND OF THE INVENTION

1. Field of the Invention

The invention pertains to the field of medicine and medical bandaging. The human body contains both soft tissue and bone. Soft tissue sometimes swells with fluids in response to various conditions or injuries. Inflammation, allergic response, surgical procedures, Arthritis, Dropsy and other conditions can cause general swelling. Injury to the forearms, wrists, hands or fingers often cause swelling of the fingers. When swelling happens to a finger the finger becomes enlarged. A ring on the swollen finger can become tight, and difficult to remove. The ring further reduces blood flow to the swollen finger resulting in pain and discomfort. In this case, the ring must be removed.

There are also times when a ring may need to be removed for medical diagnostics. When performing an MRI, all metal must be removed before the patient is placed in the machine. Another reason for removal is surgery. Some surgeries such as heart surgery can cause general body edema, or swelling. If the swelling is too great the ring can cause loss of blood flow to the finger resulting in gangrene.

For these and other reasons, removal of a ring is often necessary, but difficult. A device and method are disclosed to safely remove a ring from a swollen finger without damaging the ring.

2. Description of Related Art

Lubrication method—One common method of removing a stuck ring is to apply lubrication to the finger. This helps the ring slide over the flesh and can help reduce further trauma and inflammation. This only works if the inflammation is not too advanced, as it does not reduce the swelling in the finger.

Destructive method—The ring is cut allowing it to be pried open and removed without sliding it over the swollen finger. This has the obvious disadvantage of damaging the ring. It only works if the ring is made from a material that can be cut. Some newer jewelry is made from very hard carbide tungsten, and would be very difficult to remove with this method. The finger may be injured by the tool cutting the ring as the ring is cut.

String method—A string is wrapped around the finger beginning at the distal end of the finger and proceeding toward the ring to be removed. When the ring is reached, the end of the string is tucked under the ring. The string is then unwrapped from behind the ring, and the unwrapping string forces the ring off the finger. This method is difficult to master. The tension of the string, spacing and technique of unwrapping must be correct for the technique to work effectively. This method is of limited use for persons with arthritis. The string itself can dig into the skin, resulting in discomfort or even injury.

Surgical Glove Method—Using the finger section from a surgical glove, the finger section is pulled over the finger, feeding the glove under the ring. The ring is then slid over the glove and off the finger. It can be very difficult to feed the glove under the ring. Surgical gloves are not particularly strong and often tear when removing the ring. As in the string method, this method is of limited use for persons with arthritis. The surgical glove does not allow for adjustment or control of the pressure required for reducing the swelling of the finger.

BRIEF SUMMARY OF THE INVENTION

The problem of removing a ring from a swollen finger is solved by forming a compressible cylindrical assembly around the finger and under the ring, then compressing the cylindrical assembly and the enclosed finger to reduce swelling allowing removal of the ring. A medical kit for performing the procedure is provided.

REFERENCE NUMERALS IN DRAWINGS

15 Top (and Bottom) panel
16 Outer Skin
17 Internal Arch
18 Cutout
19 Hand-Side Retainer
21 Feeder Loop
23 Side Panel
25 Compression Tape
27 Compression Tape Puller
28 Puller Skin
29 Compression Tape Puller Insert Loop

DETAILED DESCRIPTION OF THE INVENTION

A procedure and associated medical kit are disclosed for removing a ring from a finger. In the preferred embodiment the procedure uses a compression ribbon, a compression tape puller, and a panel set.

DEFINITION OF TERMS

Figure 7:
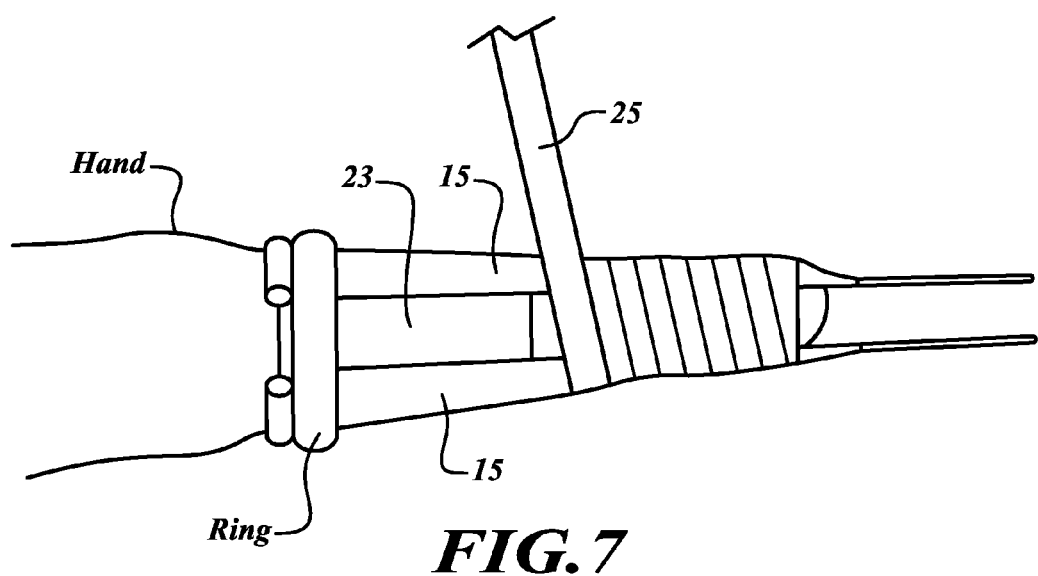
FIG. 7 shows the preferred embodiment of the ring remover assembled with the compression tape partially applied.
Figure 8:
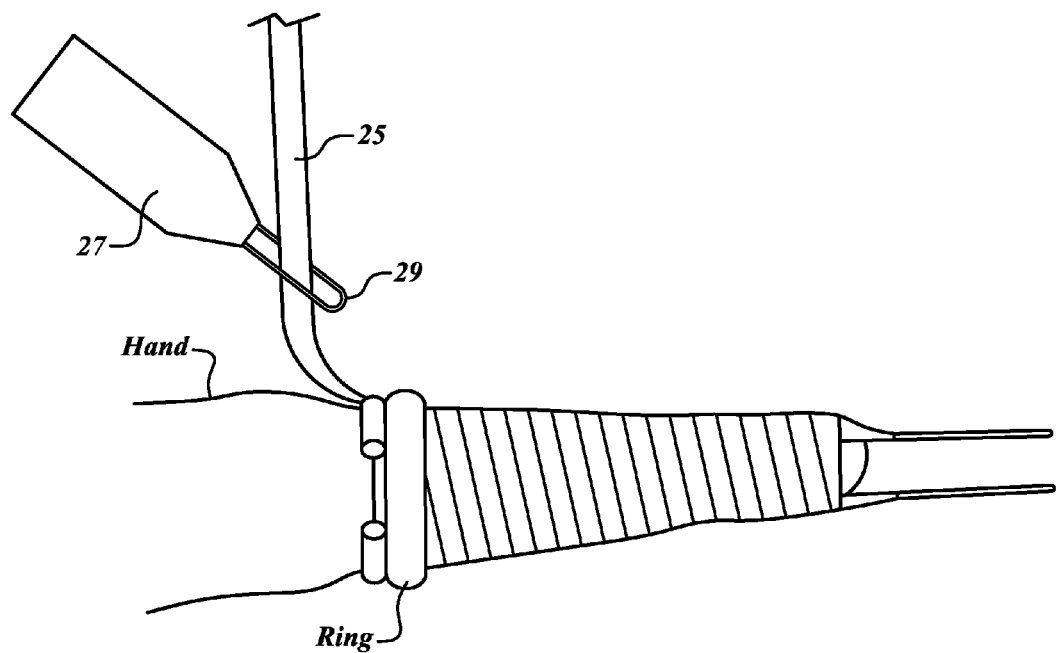
FIG. 8 shows the preferred embodiment of the ring remover fully assembled with the compression tape fully applied and drawn under the ring with the compression tape puller.

Compression Tape—A compression tape is a length of thin ribbon-like material used to reduce swelling of the finger when wrapped in a coil around the finger as shown in FIGS. 7 and 8. The required length and width depend on the size of the finger being treated.

Figure 2:
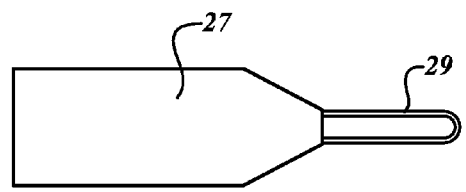
FIG. 2 shows the compression tape puller used to draw the compression tape under the ring.
Figure 3:
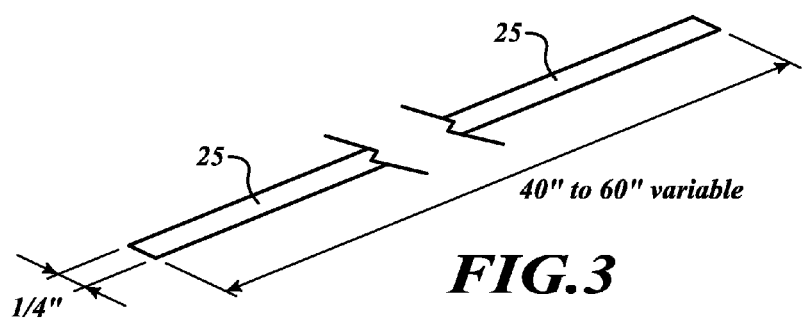
FIG. 3 shows the compression tape.

Compression Tape Puller—A compression tape puller is a tab and loop assembly as shown in FIG. 2 for pulling the end of the compression tape under the ring.

Panel—A panel is defined as an elongated piece of thin sheet material shaped in a way to conform to and partially encircle a finger under treatment. The desired size and shape of a panel is determined by the size of the finger. The width of the panel is between 0.5 and 2.0 times the diameter of the finger being treated. The length of the panel is at least long enough to extend from the ring to a point past the knuckle that is preventing the ring from being removed.

Figure 6:
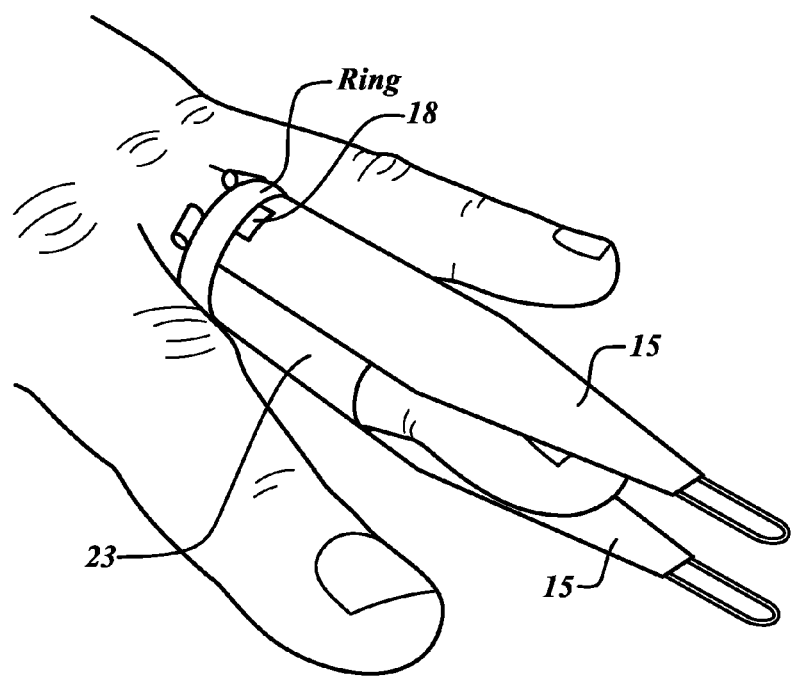
FIG. 6 shows the four panels of the preferred embodiment placed on the finger being treated thereby forming a cylindrical assembly before the compression tape is applied.

Panel set—A panel set is a plurality of panels such that when the panels are assembled around the longitudinal axis of the finger they encircle the finger forming a cylindrical assembly around the finger. The preferred embodiment of this is shown in FIG. 6. In another embodiment, the panel set may cover only a majority of the circumference of the finger, while still providing sufficient support for the compression tape. In both embodiments, the cylindrical assembly reduces in diameter as the compression tape is applied as shown in FIG. 7, allowing for removal of the ring.

Description of Kit Components

The medical kit includes a compression tape, a compression tape puller, and a panel set. In the preferred embodiment the panel set contains four panels; a top panel, a bottom panel, and two side panels.

In the preferred embodiment, the compression tape (25) is a thin strip of ribbon-like material 6.35 mm (0.25 inches) wide. Other widths between 3 mm and 13 mm are also effective and may be used. The length of the compression tape should be long enough to wrap the finger from the distal end to the ring to be removed, and have sufficient additional length to be inserted under the ring and pulled through by the person performing the procedure. In the preferred embodiment, the compression tape has a length between 100 cm and 150 cm. The compression tape may be longer or shorter than this as the width of the tape changes the required number of wraps on the finger. This expands the preferred range of length to between 25 cm and 200 cm. One of ordinary skill will note there is no absolute limit to the length of the compression tape. The compression tape should be less than 1 mm thick, and should be as thin as possible while still preserving sufficient strength to remove the ring.

The compression tape puller (27) is a pull tab and loop assembly used to draw the compression tape (25) under the ring as shown in FIG. 8. When wrapping the finger with the compression tape (25), and upon reaching the ring to be removed, the compression tape puller insert loop (29) is inserted under the ring from the hand side of the ring. The end of the compression tape is then placed through the exposed loop. Finally the compression tape puller (27) is withdrawn toward the hand pulling the compression tape end under the ring.

Figure 1:
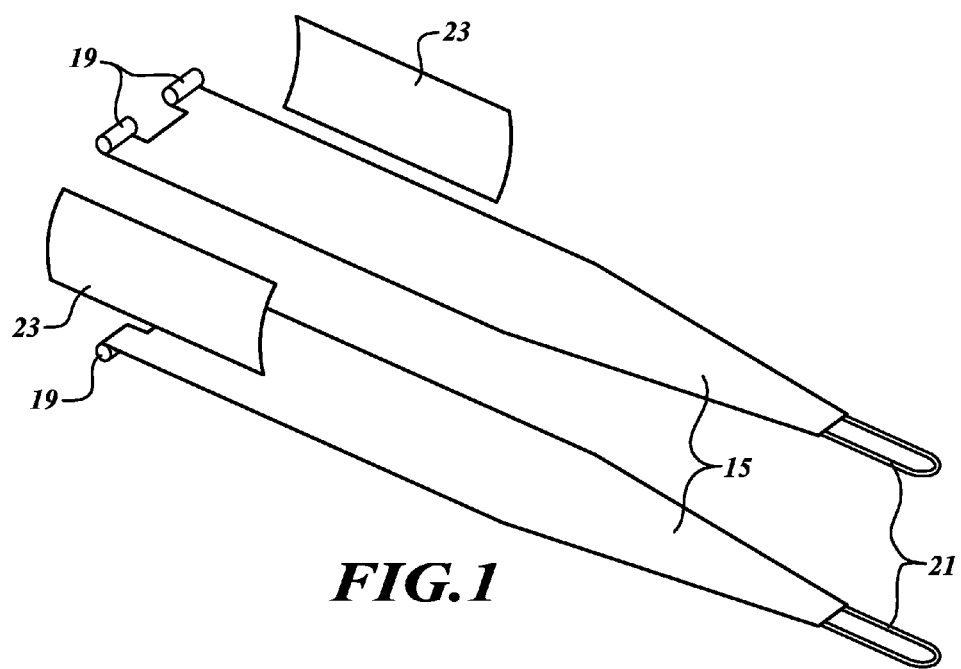
FIG. 1 shows the panel set provided in the preferred embodiment, in roughly the position they would be when placed on a finger to be treated.
Figure 4:
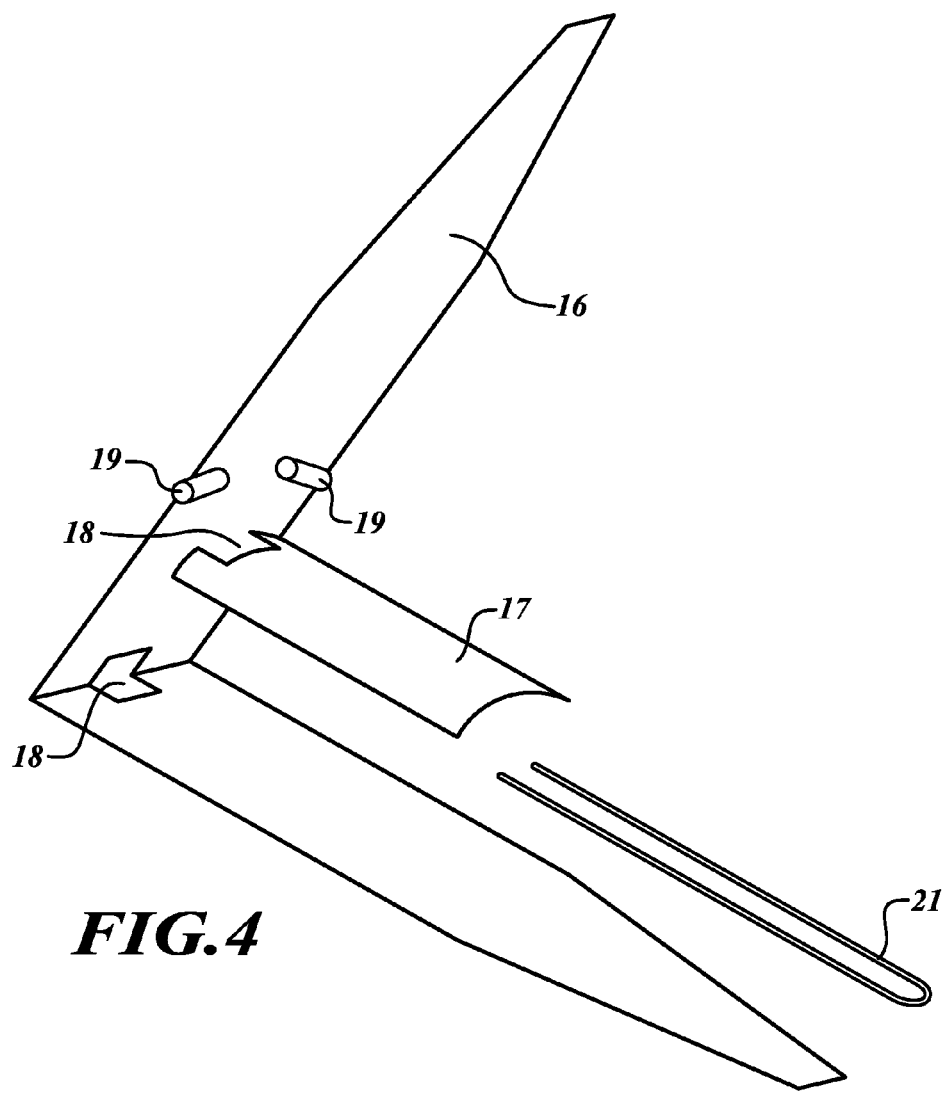
FIG. 4 shows the construction of the top (and bottom) panel in the preferred embodiment.

The preferred embodiment uses a panel set with two panel designs illustrated in FIG. 1 items (15) and (23). The top and bottom panels (15) are identical. The top and bottom panels (15) are constructed from a smooth flexible sheet material such as paper, Tyvek (a brand name paper made from flash spun high-density polyethylene fiber), fabric, high tensile cloth, polypropylene laminate, Polytetrafluoroethylene (PTFE commonly known as Teflon) composite, plastic, or synthetic material. In addition laminated combinations of these or other equivalent materials are acceptable. It is preferred that the material be as thin as possible while retaining sufficient strength and rigidity, as the ring must slide over the panels to be removed. The top and bottom panels are arched around the longitudinal axis as shown in FIG. 4 to conform to the shape of the finger. Both top and bottom panels have a narrow end and a wide end. The narrow end of the top and bottom panels is intended to be inserted under the ring from the hand-side of the finger. A feeder loop (21) is attached to the narrow end to facilitate drawing the panel under the ring from the hand-side. The hand-side retainer (19) prevents the panel from accidently sliding entirely out from under the ring as the panel is pulled toward the distal end of the finger.

There are two identical side panels shown in FIG. 1 items (23) in the preferred embodiment. They are arched, around the longitudinal axis to conform to the finger. In the preferred embodiment the side panels are made from thin smooth plastic, but may be made from any thin sheet material such as paper, Tyvek, fabric, high tensile cloth, polypropylene laminate, Polytetrafluoroethylene (PTFE commonly known as Teflon) composite, synthetic material, laminated combinations of these or other equivalent materials having similar properties.

When assembled on the finger the panel set forms a constricting cylinder assembly supporting the compression tape as shown in FIG. 7.

Alternative panel embodiments may be designed to be placed on the finger in front of the ring, inserted under the ring from the distal end of the finger, or inserted under the ring from the base of the finger. For panels that are inserted under the ring, a loop, hole, hook or tapered end may be provided to assist in drawing the panel under the ring. In the preferred embodiment, a feeder loop (21) is attached to a tapered end of the panel as shown in FIG. 1. For panels intended to be inserted under the ring from the hand side and drawn to the distal end of the finger, the preferred embodiment includes a hand-side retainer (19) to avoid pulling the panel entirely under the ring. The hand-side retainer (19) is shown in FIG. 1 on the top and bottom panels of the preferred embodiment. The preferred embodiment uses four panels, but different numbers of panels may be used as long as they can form the required cylinder assembly around the finger.

Construction of the Preferred Embodiment

The components of the kit are constructed as follows:

The top panel and bottom panel are identical with similar construction. Each top and bottom panel (15) consists of an outer skin (16) of Tyvek paper, a monofilament feeder loop (21), an internal arch (17) made of thin arched plastic or synthetic material, and two dowel sections (19) approximately ⅛ inch in diameter. The dowel sections (19) have a length equal to about ⅓ the width of the top panel as shown in FIG. 4. When assembled, the dowel sections provide space for the cutout (18). The dowel sections are aligned with the fold line of the outer skin (16) with their ends justified at the outer edges of the outer skin (16) leaving a space between the two dowel sections. The internal arch (17) is centered laterally on the outer skin (16) and adjacent to the dowel sections that create the hand-side retainer (19). The outer skin (16) is folded at its midpoint and laid back over itself to form a sandwich enclosing the internal arch (17), hand-side retainer (19), and ends of the feeder loop (21). An adhesive applied to the inner surface of the outer skin (16) secures the outer skin to itself and the internal components. Note that there is a cutout (18) near the fold line of the outer skin shown on FIG. 4. When assembled, this cutout (18) results in a space used for pulling the compression tape (25) under the ring. The assembled top and bottom panels (15) are shown in FIG. 1.

There are two identical side panels (23) in each kit. Each side panel (23) is constructed from a thin rectangular arched sheet of plastic or synthetic material 6.35 mm (0.25 inches) shorter than the internal arch used in the corresponding top and bottom panels.

The compression tape (25) is made from a ribbon of synthetic material 6.35 mm (0.25 inches) wide by 100 cm (40 inches) long. Alternatively, it may be cut from a sheet of nylon, rayon, vinyl, or other synthetic material having sufficient tensile strength. The ribbon may be longer or shorter depending on the size of the finger being treated.

Figure 5:
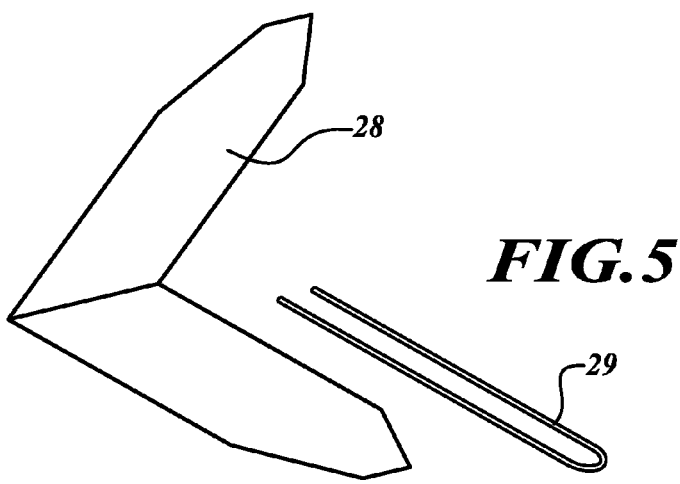
FIG. 5 shows the construction of the compression tape puller.

The compression tape puller (27) shown in FIG. 2 is constructed as shown in FIG. 5. The compression tape puller (27) is formed from a puller skin (28) made from paper, light weight cloth, fabric, or synthetic sheet material, and a monofilament puller insert loop (29). The puller skin is folded at its midpoint as shown in FIG. 5 enclosing the puller insert loop (29). Adhesive applied to the inner surface of the puller skin secures the puller skin (29) to itself and to the puller insert loop (29).

How to use the Preferred Embodiment

The problem of removing a ring stuck on a swollen finger is solved by compressing the finger under the compression tape and panel set thereby reducing the swelling and allowing removal of the ring. It is primarily for use by medical professionals but may be used by any layman in a first aid situation.

The caregiver begins by placing the panel set on the swollen finger. The top panel (15) is placed on the back of the hand in line with the finger and with the arch of the panel conforming to the finger. Next the feeder loop (21) is inserted under the ring from the hand-side on the back of the finger. Using the feeder loop (21), the top panel (15) is then pulled under the ring toward the distal end of the finger until the hand-side retainer (19) makes contact with the ring.

The bottom panel (15) is placed on the opposite side of the finger with a similar procedure. Place the bottom panel (15) on the palm of the hand aligned with the finger and the arch of the panel conforming to the finger. Insert the feeder loop (21) under the ring on the palm side of the finger. Using the feeder loop (21), pull the bottom panel (15) under the ring and toward the distal end of the finger until the hand-side retainer (19) makes contact with the ring.

After the top and bottom panels (15) are in place, the side panels (23) can be placed. The side panels (23) are placed from the distal end of the finger, one on each side between the top and bottom panels (15). The two side panels are inserted under the ring and under the top and bottom panels (15) as shown in FIGS. 6 and 7. The side panels are placed such that the arch of the side panels conforms to the curvature of the finger.

When properly placed, the side panels, together with the internal arch of the top and bottom panels form a compressible cylinder assembly encircling the portion of the finger trapping the ring as shown in FIG. 6.

After the panel set is placed, the caregiver can apply the compression tape (25). Wrap the compression tape (25) tightly around the finger beginning from the distal end of the finger and proceeding toward the ring to be removed as shown in FIG. 7. Overlap the compression tape (25) on itself up to 50 percent of the width of the compression tape when wrapping the finger. This forces the fluid from the finger back into the hand. As the compression tape (25) encounters the cylinder assembly created by panel placement proceed by wrapping the compression tape over the cylinder assembly. This reduces the diameter of the cylinder assembly returning the finger to its normal size. Continue wrapping the compression tape (25) until the ring is reached as shown in FIG. 8. Insert the compression tape puller loop (29 under the ring from the hand side in the space provided by the hand-side retainer (19). Place the end of the compression tape (25) through the compression tape puller loop (29). Pull the compression tape puller (27) away from the ring drawing the end of the compression tape (25) under the ring as shown in FIG. 8. Although anyplace may be used for inserting the compression tape puller loop (29) under the ring, there is a gap provided between the hand-side retainer (19) sections of the top and bottom panels (15) for this purpose.

Figure 9:
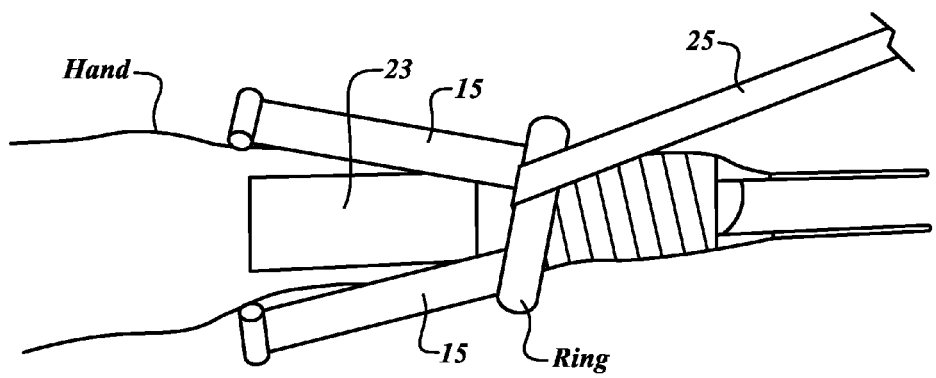
FIG. 9 shows the preferred embodiment of the ring remover fully assembled about the finger with the ring partially removed, the compression tape in the process of being unwound thereby removing the ring.

With the end of the compression tape (25) on the hand side of the ring and the finger returned to normal size, the caregiver pulls on the end of the compression tape (25) in the direction of the finger tip. As the compression tape unwinds, the ring is pulled over the panels and off the end of the finger as shown in FIG. 9. Unrestrained by the ring and compression tape, the panels fall off the finger, and the procedure is complete.

SUMMARY AND ADVANTAGES OF THE INVENTION

The problem of removing an in-tact ring over a swollen finger is solved by recognizing that swelling must be reduced by the application of pressure to the finger. The preferred embodiment distinguishes itself from the prior art by using a combination of components to distribute pressure to the finger more efficiently. A cylindrical assembly is constructed around the finger and under the ring that covers the finger from the ring to a point past the knuckle that is preventing the ring from being removed. As the compression tape is applied, the cylindrical assembly is compressed, and its diameter is reduced. The pressure applied is focused in a circle, matching the interior shape of the ring. In the prior art, the various tissues of the finger are forced equally, even if they do not contribute to shrinking the effective diameter of the finger. Maintaining an efficient cylinder shape while compressing the finger reduces pain and facilitates the flow of body fluids in a more efficient manner. The best mode construction of the cylindrical assembly uses a series of panels as shown in FIG. 6 and described above. The panels should be as thin as possible and preferably less than 1 mm thick. Different numbers of panels may be used by applying the principles evident in this disclosure to'perform the same function.

In one version of the prior art, a string is applied to the finger to compress the tissues and remove the ring in a manner similar to the method disclosed with the compression tape. The tape or string must be thin enough to slide under the ring, as the ring must slide over either to be removed. This limits the thickness of the string or ribbon to less than 1 mm. Even a 1 mm thick string will dig into the skin of the finger deeply when wrapped tightly. By contrast, a ribbon can be far thinner, 0.1 mm or even less, and still maintain enough strength to be handled if it is wide enough. Therefore the ribbon requires less clearance for removing the ring. This has the additional benefit of distributing the pressure on the finger over a wider area and does not damage the skin of the finger.

One feature of interest is the space provided on the wide end of the top and bottom panels as shown in FIG. 4. The small square cutout (18) at the fold line creates a space between the two pieces of the hand-side retainers. This space can be seen in figure six as being just behind the ring on the finger being treated. This space allows for the compression tape puller loop (29) to be inserted under the ring at this point. This facilitates easily drawing the tape under the ring as shown in FIG. 8.

One embodiment is intended to be provided in kit form as individually packaged disposable kits. Because of variations in finger size, different kits adapted to different size fingers are necessary. Alternatively, composite kits containing multiple sizes may be used. A set of instructions may also be included.

I claim:

1. A medical kit for the removal of a ring from a swollen finger comprising:
   a plurality of elongated panels including at least one first panel;
   said first panel having a leading portion and a trailing portion;
   a hand side retainer coupled to said trailing portion, wherein said hand side retainer is a dowel retained in a seam formed by a fold in said first panel;
   a cutout located on an edge of said trailing portion, bisecting said hand side retainer, and configured to create a space between said ring and said finger when said first panel is positioned between said ring and said finger; and
   a compressing means for applying pressure to said finger over said plurality of elongated panels.

2. The medical kit of claim 1 wherein said first panel includes a feeder loop coupled to said leading portion.

3. The medical kit of claim 1 wherein said compressing means is a string.

4. The medical kit of claim 1 wherein said compressing means is an elastic sleeve.

5. The medical kit of claim 1 wherein said compressing means is a compression tape.

6. The medical kit of claim 5 further comprising a compression tape puller having a pull tab and compression tape puller insert loop coupled to said pull tab.

7. The medical kit of claim 1 wherein said hand side retainer is a stop coupled to said first panel, and configured to prevent said first panel from sliding entirely under the ring when said first panel is inserted between said ring and said finger from the hand side and pulled toward the distal end of said finger.

8. A method of removing a ring from a swollen finger comprising the steps of:
   covering a portion of said finger with a first panel by inserting said first panel between said ring and said finger from a hand side of said finger and drawing said first panel toward a distal end of said finger;
   wrapping a compression tape around said finger and over said first panel;
   and removing said ring over said compression tape and said first panel.

9. The method of claim 8 further comprising the steps of:
   inserting an end of said compression tape under said ring after wrapping said finger with said compression tape; and
   pulling said end of said compression tape toward the distal end of said finger thereby removing said ring from said finger and unwrapping said compression tape.

10. The method of claim 9 wherein:
    the step of covering a portion of said finger with said first panel further includes positioning a cutout between said ring and said finger thereby creating a space under said ring; and
    the step of inserting said end of said compression tape under said ring is accomplished by inserting said end of said compression tape through said space.

11. A ring remover comprising:
    an elongated panel having a leading portion and a trailing edge, the elongate panel configured to be placed between a ring and a finger;
    said leading portion being less than 1 mm thick;
    a hand side retainer comprising a dowel fixed to said trailing edge for retaining said elongated panel between said ring and said finger,
    a cutout located on said trailing edge, said cutout is a notch bisecting said hand side retainer; and
    a compression tape for applying pressure to said finger.

12. The ring remover of claim 11 wherein said cutout on said trailing portion is configured to create a space under said ring when said elongated panel is positioned under said ring.

13. The ring remover of claim 11 wherein said elongated panel further comprises an insertion means for feeding said elongated panel under said ring coupled to said leading portion.

14. The ring remover of claim 13 wherein said insertion means is a feeder loop.

15. The ring remover of claim 14 where said elongated panel is made from flash spun high-density polyethylene fiber.

16. The ring remover of claim 15 further comprising a compression tape puller coupled to a compression tape puller insert loop.

17. The ring remover of claim 13 wherein said insertion means is a hook.

18. The ring remover of claim 13 wherein said insertion means is a tapered end.

* * * * *